United States Patent [19]

Rappas et al.

[11] 4,047,940

[45] Sept. 13, 1977

[54] SEPARATION AND RECOVERY OF COPPER METAL FROM AMMONIACAL SOLUTIONS

[75] Inventors: Alkis S. Rappas, Arlington; J. Paul Pemsler, Lexington, both of Mass.

[73] Assignee: Kennecott Copper Corporation, New York, N.Y.

[21] Appl. No.: 695,389

[22] Filed: June 14, 1976

[51] Int. Cl.$^2$ ............................................. C22B 15/12
[52] U.S. Cl. ...................................... 75/108; 75/.5 A; 75/117; 204/106; 204/108; 423/42
[58] Field of Search ................. 204/108, 106; 75/108, 75/117, .5 A; 423/42

[56] References Cited

U.S. PATENT DOCUMENTS

| | | | |
|---|---|---|---|
| 2,440,612 | 4/1948 | Lichtenwalter | 75/117 |
| 3,844,763 | 10/1974 | Burkin | 75/.5 A |
| 3,865,580 | 2/1975 | Hummel et al. | 423/32 |
| 3,865,744 | 2/1975 | Parker et al. | 252/188.3 R |
| 3,883,351 | 9/1974 | Neskora et al. | 75/.5 A |
| 3,937,657 | 2/1976 | Parker et al. | 204/108 |
| 3,961,028 | 6/1976 | Parker et al. | 423/41 |
| 3,966,890 | 6/1976 | Parker et al. | 423/512 A |
| 3,983,017 | 9/1976 | Szabo | 204/106 |

*Primary Examiner*—G. Ozaki
*Attorney, Agent, or Firm*—John L. Sniado; Anthony M. Lorusso

[57] ABSTRACT

Copper is recovered from solutions containing cupric ammoniacal complexes by reducing copper in the complexes to the cuprous state and thereafter precipitating the copper as cuprous acetylide by passing acetylene through the solution. After the cuprous acetylide is separated from the solution and washed thoroughly, it is reacted with acetonitrile and an acid to form acetylene and a cuprous-acetonitrile complex: $Cu(CH_3CN)_2^+$. The solution containing this complex is then flash distilled to remove the acetonitrile and to disproportionate unstable cuprous ions into copper metal and cupric ions. Following the disproportionation, the components are separated and copper metal is collected.

32 Claims, 3 Drawing Figures

SEPARATION AND RECOVERY OF COPPER METAL FROM AMMONIACAL SOLUTIONS

BACKGROUND OF THE INVENTION

This invention relates to the recovery of copper from ammoniacal solution which may also contain nickel, cobalt, and other ions. In practicing the invention, very pure copper metal is obtained without the need to employ ion exchangers, acid stripping, electrowinning, or electrorefining.

It is known that copper (as well as nickel and cobalt) can be leached from the ores with ammoniacal leach liquors. One method of separating the copper values from such leach liquors while leaving the nickel and other metals in the raffinate, is disclosed in U.S. Pat. No. 2,440,612 to M. Lichtenwalter entitled *Separation of Copper*. In accordance with the process disclosed therein, the copper is recovered from the ammoniacal leach solutions by first reducing the copper values to the cuprous state and then precipitating the reduced copper by reacting it with acetylene to yield insoluble copper actylide which may be separated from the solution by filtration. If silver, mercury, or gold components are present in the leaching solution with the copper, these will also be precipitated out.

In addition to the above process, it is known that solutions of cuprous salts can be thermally or electrochemically disproportionated to produce copper and solutions of cupric salts. This method is disclosed in U.S. Pat. No. 3,865,744 to Alan J. Parker et al. In general, this method involves reacting a cuprous salt with a ligand, i.e., an organic nitrile, to form a cuprous nitrile complex such as $Cu(CH_3CN)_2^+$. The solution containing the complex can then be distilled to produce copper powder, a cupric salt, and an organic nitrile.

The present invention provides a method of isolating and purifying copper utilizing a novel combination of the above two known copper recovering processes.

SUMMARY OF THE INVENTION

The process of the present invention produces copper metal from an ammoniacal solution containing cuprous ions. The process comprises the steps of precipitating the cuprous ions from the ammoniacal solution as a cuprous acetylide, separating and washing the cuprous acetylide precipitate, acid hydrolyzing the cuprous acetylide in the presence of a cuprous ion stabilizing ligand, e.g., a nitrile, and disproportionating the resulting cuprous complex to produce copper metal and cupric salt.

The process of the present invention is characterized by the use of reactions which take place at or near ambient temperatures and pressures, and thus a system for utilizing the process can be built at a relatively low cost. In addition, many of the reagents in the process can be recycled, allowing further cost savings, and the process is quite energy efficient. Also, upwards of 99% of the available copper can be recovered and the product metal is of very high purity.

Accordingly, it is an object of the present invention to provide a process for obtaining pure copper from ammoniacal copper containing solutions which avoids the necessity of electrowinning the copper, is capable of continuous operation on an industrial scale with a relatively low capital outlay, involves reactions which occur at or near ambient temperatures and pressures, and employs reagents which are neither unduly corrosive nor consumed.

Another object of the invention is to provide such a copper recovery process which is energy efficient and significantly diminishes the quantities of waste involved when compared with prior art processes by regenerating and recycling reagents.

Still another object of the invention is to quantitatively separate copper from ammoniacal solutions containing copper and other metals such as nickel, cobalt, iron, manganese, etc., without using an ion exchanger.

Another object of the invention is to produce copper of very high purity by precipitating cuprous ions from solutions as a cuprous acetylide, separating the cuprous acetylide precipitate, reacting the acetylide with an acid and a nitrile to form a cuprous-nitrile complex, and disproportionating the cuprous ion to produce copper metal.

DESCRIPTION OF THE PREFERRED EMBODIMENTS

Figure 1:
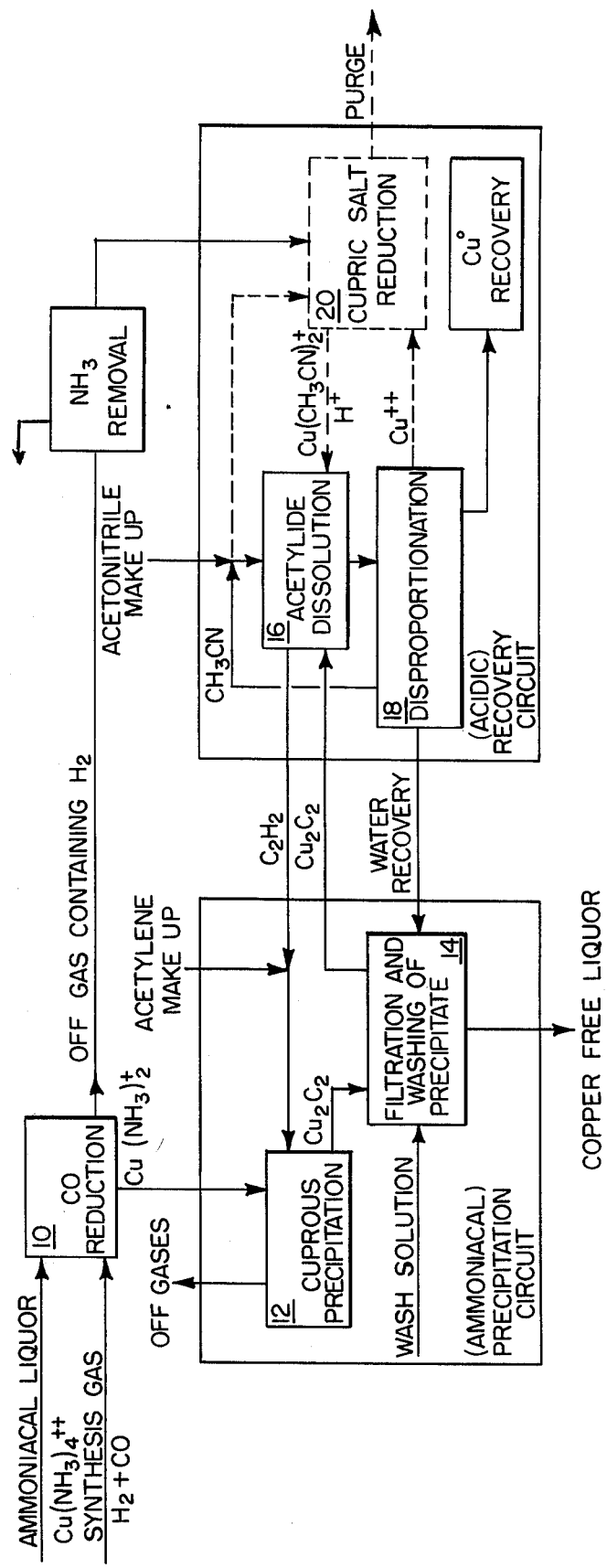
FIG. 1 is a schematic flow diagram illustrating one important embodiment of the process of the invention as it is used in the recovery of metallic copper from an ammoniacal leach solution.

At the outset the invention is described in its broadest overall aspect with a more detailed description following. The present invention is a process for obtaining copper from ammoniacal leach liquors containing copper values, anions such as $OH^-$, $Cl^-$, $SO_4^=$, $NO_3^-$, $C_2H_3O_2^-$, $CO_3^=$, $HCO_3^-$, $HPO_4^=$, $H_2PO_4^-$, $PO_4^\equiv$, and mixtures thereof, and possibly other base metal values such as nickel, cobalt, molybdenum, etc. A representative source of of an ammoniacal leach liquor containing copper as well as nickel, cobalt, and molybdenum values is the pregnant liquor obtained from the leaching manganese nodules. For details of such a leaching process, see U.S. Pat. No. 3,983,017 to Lester J. Szabo, entitled Recovery of Metal Values from Manganese Deep Sea Nodules using Ammoniacal Cuprous Leach Solutions, filed Feb. 10, 1975, the teachings of which are incorporated herein by reference.

One reason why the leach liquor of nodule processes can be advantageously treated by the present process to recover copper values is that the copper values are present in a reduced cuprous state. However, the present process can be employed to great advantage when treating other ammoniacal leach liquors, so long as the copper values are reduced to the cuprous state. Thus, an ammoniacal leach liquor containing cupric copper and possibly other metal values may be reduced with a reducing agent such as synthesis gas to produce the cuprous amine complex in solution. Alternatively, an aqueous ammoniacal cupric solution may be reduced by intimately contacting an inert organic phase containing an organic reducing agent, of the type known to those skilled in the art, with the aqueous phase to produce the cuprous solution. It should be noted that the cuprous ligand complex, $Cu[Lg]_2^+$ (where Lg is the ligand), is the starting point for the process of the present invention. A particular system for the production of this complex forms no part of the invention. A well known complex is the cuprous ammine complex, $Cu(NH_3)_2^+$.

In practicing the invention, the ammoniacal leach liquor containing cuprous ions is contacted with acetylene to precipitate the copper values as cuprous acetylide. The acetylide is then reacted with acetonitrile and a mineral acid to form acetylene and a cuprous-acetonitrile complex, e.g., $Cu(CH_3CH)_2^+$. The cuprous-acetonitrile complex is disproportionated into copper metal and cupric ions. Following this step, the copper metal is collected. The cupric ions form salts of the acid used during the hydrolysis of the cuprous acetylide. This solubilized salt may be recycled.

The presently preferred method for preparing the cupric ions produced as a byproduct of disproportionate for recycle is a novel hydrogen reduction disclosed in U.S. Ser. No. 695,390 entitled, *Low Temperature and Pressure Continuous Reduction of Copper in Acid Solutions* by A. S. Rappas and J. P. Pemsler, filed on even date herewith. If hydrogen is used for the cupric reduction to cuprous complex, then the cuprous complex may be recycled to the acid hydrolysis of cuprous acetylide step since the solution will contain, aside from the complex, only hydrogen and, e.g., sulfate ions. These hydrogen ions will leave the acid cycle of the process as acetylene when this is regenerated from the acetylide, and thus the acidity of the system may be easily controlled at desirable levels.

The acetylene and acetonitrile may be contained in separate closed systems and recycled. Sulfuric acid may also be contained in a closed system and recycled if the last reduction is done with hydrogen gas and the nitrile complex produced is recycled to the dissolution of acetylide before distillation as outlined above.

The acetylene is reclaimed during the formation of the cuprous complex in the acidic solution, and reused in the precipitation step. In like fashion, the ligand, e.g., nitrile, preferably acetonitrile, used in the formation of the cuprous complex to be disproportionated, is reclaimed during the disproportionation step and recycled. It is preferred to utilize sulfuric acid during the hydrolysis of cuprous acetylide. However, any mineral or organic acid of adequate strength which does not form an insoluble precipitate or complex with the cuprous ion may be used in this step. Dilute nitric acid can be used if the pH of the solution is controlled.

Referring to FIG. 1, in the first step of the process, the solution containing the cuprous ions is transferred to precipitattion tank 12.

As is stated above, processes exist which produce cuprous ions. On the other hand, it may be necessary to produce cuprous ions by reducing cupric ions. If synthesis gas is used for the above reduction to cuprous ammonia complex, the off gas will be hydrogen rich and may be recovered for use in the recycle of cupric sulfate as is shown in the drawing. If the cuprous ions are produced in reactor 10, the residence time in reactor 10 should be adjusted so that complete conversion to cuprous is effected. The reduction with carbon monoxide is pH sensitive, as is well known, and the reduction rate depends on the concentration of cuprous ion present in solution. This dependence indicates that the reaction must be initiated by formation of cuprous ions by some other means, e.g., by addition of some copper metal into the reactor, before the reduction with CO commences. The pH range is between 9 and 12 in this case, and it can be controlled by adjusting the ratio of carbon dioxide to ammonia. The temperature should be maintained below 70° C to minimize ammonia losses. In carbonate systems, the reduction can be performed at a carbon monoxide pressure close to atmospheric pressure. In an ammoniacal sulfate system, the reduction to cuprous ammine can be effected with $SO_2$, as known.

Acetylene, compounds which produce acetylene, or an acetylenic compound having the formula $RC≡CH$, where R is an alkyl with 1-6 carbon atoms, e.g., 3, 3 dimethyl-1-butyne, is then introduced into precipitation reactor 12 and intimately contacted with the solution containing cuprous ions to precipitate a cuprous acetylide according to reactions such as:

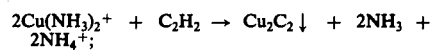

or

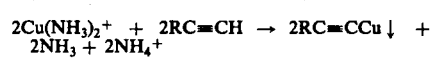

This reaction is extremely rapid, quantitative, and specific for the removal of copper from the solution and is well known in the art. If silver or mercury ions are present in solution, they will coprecipitate with the copper. All other metal ions will remain in solution. The precipitation of cuprous acetylide occurs at ambient temperatures and pressures and the precipitate is easily settled, filtered, and washed. Only a slight excess of the acetylene need be used to ensure a quantitative precipitation. Cuprous ammoniacal solutions are very good scrubbing solutions for the removal of acetylenic compounds from gases, thus the acetylenic compound content in the gas introduced into precipitation reactor 12 can be anywhere from a few tenths of one percent to one hundred percent, the balance being nitrogen, helium, argon, carbon monoxide, hydrocarbons, hydrogen, etc. Gases which oxidize cuprous, such as oxygen, should not be allowed into reactor 12. The time required for complete cuprous acetylide precipitation is thus determined by the amount of copper in solution, concentration of acetylene in the feed gas, flow rate of feed gas, and degree of contact between the gas and liquid phases. Typically, a solution residence time of 10 to 15 minutes is sufficient.

The slurried precipitate from the precipitation reactor 12 is next transferred to filtration and washing apparatus 14 where the cuprous acetylide is filtered, washed, repulped, and refiltered. Prior to filtration, the acetylide may be settled, the bulk of the solution decanted, and the thickened slurry thereafter filtered and washed as outlined above. The above handling (processing) of the wet acetylide should be done in a non-oxidizing atmosphere (not air, oxygen allowed). Copper free filtrates from filtration and washing apparatus 14 contain nickel, cobalt, and other metals which were present in the original ammoniacal liquor, which metals may be recovered by techniques know to those skilled in the art. Ammonia, ammonium carbonates, and other anions will also be present in the copper free raffinate and can be recovered by known techniques. The filtration and washing efficiency is important, not so much for copper product purity, but for minimizing or eliminating the need for a purge of the copper recovery circuit. If the reduction in reactor 10 and the precipitation in reactor 12 are properly performed to completion, then the amount of copper that is lost in the raffinate is of the order of a few parts per million.

The washed cuprous acetylide filter cake is resuspended in water and dissolved in an acidic solution of nitrile, preferably acetonitrile, in dissolution tank 16. As has been stated above, a preferred acid is sulfuric acid. The dissolution of cuprous acetylide is actually a hydrolytic dissolution. It proceeds according to the reaction.

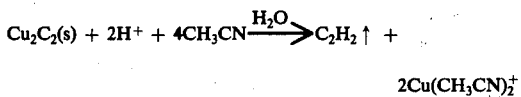

Acetylene is regenerated during this reaction and may be collected and recycled to the precipitation reactor 12. Up to 98% of the acetylene can be recovered from the cuprous acetylide for recycle and any loss can be made up by providing an acetylene makeup and introducing the gas into the recovery line as needed.

While the preferred ligand which stabilizes cuprous ions as a cuprous complex is acetonitrile, it will be obvious to those skilled in the art that other nitriles, e.g., an alkyl nitrile of the general formula RCN where R is a lower alkyl group, may be substituted for the acetonitrile as desired. Non-limiting examples of such equivalent nitriles include acrylonitrile and 2-hydroxy-cyanoethane. 2-hydroxy-cyanoethane is excellent for electrowinning embodiments.

The rate of hydrolytic dissolution of acetylide depends on pH, concentration of acetonitrile in solution, and partial pressure of acetylene. Lower pH, higher concentration of nitrile, and removal of acetylene from the reactor favor the dissolution rate. The dissolution may be carried out at atmospheric or lower than atmospheric pressure, and at temperatures ranging from ambient to about 70° C. If the dissolution is performed at atmospheric pressure, the preferred temperature is 55° C. Typical residence time in the dissolution tank 16 is 15 to 30 minutes.

The dissolution should be carried out in the absence of oxidizing gases such as oxygen. One area of concern is the possibility of some carry-over of the typically volatile nitrile from dissolution tank 16 into the precipitation circuit along with the acetylene. To prevent this, an off gas condenser or a scrubber may be provided as necessary.

If so desired the off-gas containing acetylene can be processed further to concentrate the acetylene, by known techniques, before the acetylene is recycled to tank 12.

In the next step of the process, the cuprous acetonitrile complex containing solution is transferred to a disproportionation tank 18. The solution in tank 18 is indirectly heated with, e.g., exhausted steam, and flashed in a single stage to remove acetonitrile and thus to disproportionate cuprous ions into copper powder and cupric ions according to the reactions:

Acetonitrile and water form an azeotrope, 83.7:16.3, which boils at 76.5° C at atmospheric pressure. Acetonitrile can be distilled even from dilute solutions. Thus, the overhead vapors from the flash distillation step which contain water and acetonitrile may be fractioned to remove the water, thereby maintaining water mass balance. The acetonitrile is recycled to the acetylide dissolution tank 16.

If $Cu^{++}$ ions resulting from disproportionation are recycled by first reducing them in the reduction tank 20, then acetonitrile, is also recycled to the same tank in order to stabilize the cuprous ions formed in solution. This step, which preferably employs hydrogen gas as the reducing agent, is set forth in detail in the copending patent application Ser. No. 695,390 referred to above.

An independent source of acetonitrile can be attached to the recycle line in order to make up small losses due to its hydrolysis. Optionally, a third component such as acetone, methanol, ethanol, etc. can be added, if so desired, to form a ternary azeotrope. The effect of such a third component on the dissolution of acetulide is to slightly increase the rate of hydrolysis. However, it is preferable to use only acetonitrile and water in order to facilitate mass balances and maintain control over process conditions.

The water which is removed by vapor fractionation can be recycled to the cuprous acetylide washing and repulping apparatus 14 as needed.

As indicated above, cuprous ions, destabilized by the loss of the acetonitrile, disproportionate into copper metal and cupric ions. The ratio of copper metal to copper ions in the acidic solution is determined mainly by the simultaneous equilibria:

| $2Cu^+ \rightleftarrows Cu^\circ + Cu^{++}$ | $[Cu^{++}]/[Cu^+]^2 = 10^6$ |
|---|---|
| $Cu^+ + 2CH_3CN \rightleftarrows Cu(CH_3CN)_2^+$ | $K_2 = \dfrac{[Cu(CH_3CN)_2^+]}{[Cu^+][CH_3CN]^2}$ |
| | $\log K_2 \simeq 4.35$ |

Depending on the $Cu^+/CH_3CN$ and the $CH_3CN/H_2O$ ratios, a third and fourth molecule of acetonitrile may coordinate with the cuprous ion.

Copper precipitates as a powder which is then separated from solution, and, if desired, treated by conventional technology by dewatering, drying briquetting, melting, and casting in order to obtain a more marketable product.

If sulfuric acid is chosen for use in the dissolution of acetylide step, the cupric ion formed as a result of disproportionation will be in the form of cupric sulfate. For every mole of copper metal produced during disproportionation, one mole of cupric ions is also produced, and obviously, this oxidized copper must be recovered in order for the process to have any commercial significance.

There are several theoretically feasible methods of recovery available for the cupric sulfate. For instance, copper could be recovered by electrowinning and the acid produced could be recycled to the dissolution tank 16. If this method were used, the copper produced would be copper powder and electrowon copper at an approximate ratio of 1:1. However, this recovery method would be economically unattractive and would defeat some of the objectives of this invention, e.g., the elimination of the necessity of electrowinning.

A second alternative is to introduce the cupric ions directly into the reduction reactor 10. This alternative, however, is also attended by several disadvantages, perhaps the most serious of which is that excess acid will be neutralized by the ammoniacal solution entering reactor 10, thereby forming ammonium salts which must be bled and processed. Furthermore, the cupric ion produced in the disproportionation step is fairly concentrated and consequently, it would be uneconomical to introduce it into the initial dilute ammoniacal solution. Moreover, such a course would require that the copper ions be separated again by precipitation with acetylene and redissolved in additional acid and acetonitrile. Such a solution to the recycle of cupric sulfate would require larger inventories of ammonia, acetylene, acetonitrile, and sulfuric acid; and, it would also consume more reducing gas, i.e. CO.

A third alternative would be to reduce cupric sulfate, in the presence of acetonitrile, with sulfur dioxide, in order to obtain a cuprous nitrile complex and sulfuric acid. The feasibility of this reduction scheme has been shown in the prior art literature, i.e., the Parker et al. patent referred to above. The reduction of cupric ions to a cuprous nitrile complex requires higher than atmospheric sulfur dioxide pressure, higher than ambient temperature, and most importantly, strict pH control. Most of the acid produced must be neutralized. If this alternative were chosen, the complex could be recycled to distillation tank 18 only, and not to the acetylide dissolution tank 16, since this solution would not be acidic enough to dissolve acetylide and regenerate acetylene. Accordingly, sulfuric acid would have to be added in order to dissolve acetylide and sulfate ions originating both from the sulfuric acid added and from the sulfur dioxide reduction step would have to be removed in order to satisfy a sulfate mass balance.

It would be very advantageous if cupric sulfate could be directly reduced by hydrogen gas in the presence of acetonitrile to produce a cuprous nitrile complex and sulfuric acid. Thermodynamically, this reduction is possible even at low pH's but kinetically, it requires high temperatures and pressures, and hence the use of autoclaves. It also requires a pH control system to neutralize some of the acid formed. If the pH is above about 5, reduction will proceed only so far as to precipitate $Cu_2O$. Still worse, under the necessary conditions of high temperature and pressure, the acetonitrile necessary to stabilize cuprous ions would be completely destroyed by hydrolysis.

The preferred method of recovering the $Cu^{++}$ produced during disproportionation is based on the discovery set forth in copending patent application Ser. No. 695,390 that the reduction of cupric ion to the cuprous acetonitrile complex can be accomplished at ambient temperatures and pressures, even at pH less than 1.0, with the aid of a solid hydrogenation catalyst such as palladium or platinum on an inert support. This reduction produces cuprous acetonitrile complex and acid and therefore is particularly well adapted for use in the process of this invention.

Accordingly, the cupric ions produced in disproportionation tank 18 may be delivered to reactor 20, and mixed with hydrogen and acetonitrile. In this situation, the acid produced by the hydrogen reduction in reactor 20 can be totally used to dissolve acetylide and regenerate acetylene by being introduced into dissolution tank 16. The sulfate or other acid anions can thus be contained in a closed system: hydrogen ions leaving the system via the acetylene recycle and being introduced via cupric reduction. Thus a proton build-up in the acid circuit of the process is avoided.

The coupling of acetylide dissolution described herein with the disclosed catalytic hydrogen reduction is mutually beneficial since no acid is actually being consumed in the process sulfate being contained in a closed circuit, and since the catalytic reduction can be contained in a closed system with no undesirable hydrogen ion build up. Thus, a process is provided wherein copper is quantitatively separated from relatively dilute cupric ammoniacal solutions and thereafter recovered as a very pure, copper powder product.

Feasibility of the process of the invention may be demonstrated by a series of laboratory tests using exemplary procedures as disclosed below. The apparatus used in these tests is illustrated in FIGS. 2 and 3.

Figure 2:
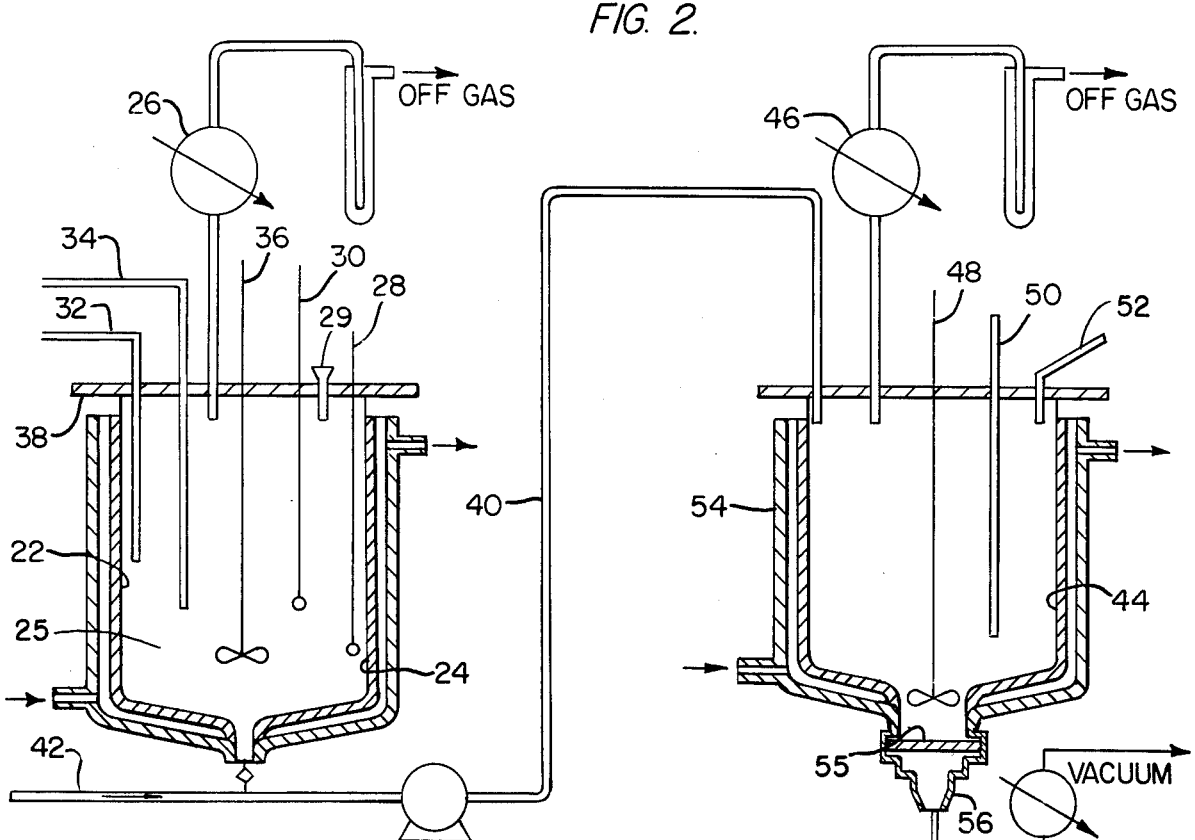
FIG. 2 is a schematic diagram of laboratory apparatus for effecting the reduction of cupric ammoniacal solutions to cuprous solution and for precipitating and collecting the cuprous acetylide.

Referring to FIG. 2, a flask 22 is shown having a water jacket 24 through which water of a desired temperature may be circulated to control the interior temperature of the reaction chamber 25. The flask 22 is supplied with a water colled reflux condenser 26, a pH detector 28, a thermometer 30, a sampling tube 29, a solution inlet 32, and a gas inlet 34. A stirrer 36 passes through the top 38 of container 22. At the bottom of the container, a conduit 40 equipped with an argon source 42, leads to flask 44. Like flask 22, flask 44 is equipped with a refluxing condenser 46, a stirrer 48, a thermometer 50, a gas inlet 52, and a water jacket 54 for temperature control. At the bottom of flask 44, a filter 55 separates the reaction chamber of the flask from an exit port 56 which leads through conduit 58 to a filtrate collecting chamber 60.

Figure 3:
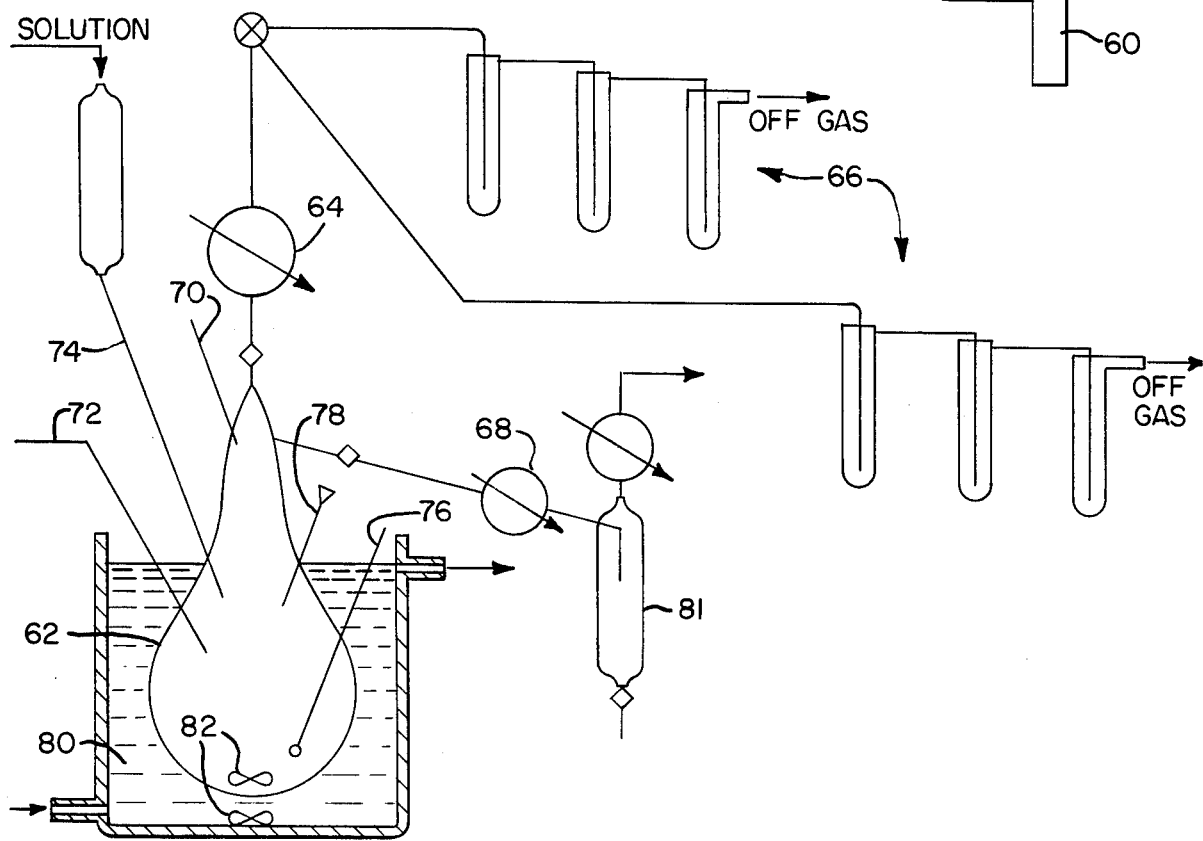
FIG. 3 is a schematic diagram of laboratory apparatus for effecting cuprous acetylide dissolution with means for disproportionating cuprous acetonitrile complex to form copper powder and cupric ions, as well as for scrubbing the acetylene gas produced.

Referring to FIG. 3, apparatus for converting cuprous acetylide to the cuprous acetonitrile complex and for disproportionating the complex is shown. This apparatus comprises a four neck round bottom flask 62 equipped with a water cooled reflux condenser 64 which leads to a pair of alternately usable acetylene scrubbing systems 66. In addition to the four necks, the flask is equipped with a spiral condenser 68, usable alternatively with the refluxing condenser 64 and collection flask 81, and a neck thermometer 70. The four necks of the flask are used as an argon inlet 72, a solution inlet 74, a reaction flask thermometer 76, and a sampling tube 78. The flask rests in a temperature controlled water bath 80 and contains a pair of magnetic stirrers 82.

EXAMPLE 1

Approximately 13.4 g of basic cupric carbonate (55.9% assay as Cu) and 10 g of ammonium carbonate are together dissolved in 300 ml of ammonium hydroxide (30% $NH_3$), and water is added to bring the total volume to 1 liter. The dark blue ammoniacal solution is introduced through solution inlet 32 into flask 22 for reduction with carbon monoxide. The temperature within flask 22 is kept constant at 45± 2° C, and the pH of the solution is adjusted to 10.5 by controlling the relative amounts of ammonia and/or carbon dioxide introduced through gas inlet 34. The air initially in the flask is displaced with carbon monoxide introduced through port 34 and the off-gases are passed through a gas flow indicator (not shown). Stirring commenses when the air is completely displaced from the flask. A piece of copper wire, which has previously been cleaned by dipping in nitric acid solution, is introduced into the flask to initiate the reduction of cupric to cuprous. With a small positive flow of carbon monoxide maintained through the flask, the progress of the reduction is monitored by withdrawing samples of solution through sampling port 29 with a gas tight syringe.

The test samples removed are assayed for cuprous ion by being subjected to oxidation with a ferric soluiton, and thereafter titrating the resulting ferrous ions produced with a standard cerric solution.

When the reduction is complete, 600 ml of the colorless cuprous solution (containing 4.7416 g of copper) is pumped to flash 44 through conduit 40, while maintaining a low argon flow rate through argon supply 42 to prevent oxidation. Prior to introducing the cuprous solution into flask 44, the air therein is displaced with carbon monoxide introduced through gas inlet port 52. With the 600 ml sample of cuprous solution in flask 44, pre-purified acetylene gas is introduced through gas inlet 52 and the solution is stirred moderately. The reaction between the cuprous ions and acetylene is almost instantaneous at the temperature employed, i.e., 25° to 30° C.

In a few minutes, precipitation of cuprous acetylide is complete employing only a small positive flow of acetylene gas and moderate stirring. The slurry is then filtered through filter 55 under an argon atmosphere, the filtrate being collected in collecting chamber 60 and analyzed by atomic absorption to determine the amount of copper left in the solution. The filter cake which collects on filter 55 is washed with 200 ml of a dilute ammonia solution (pH 9.0-9.5) and the wash solution is analyzed by atomic absorption to determine percent copper in the wash solution. The amount of solid in the filter cake is determined by dissolving a weighed amount of the wet acetylide in HCl and analyzing the solution for copper. The amount of solid is calculated assuming that all copper in the solid is present as $Cu_2C_2$.

28.80 g of the filter cake obtained as disclosed above is then transferred into the four necked, round bottom flask 62. The handling of the wet cuprous acetylide is conducted such that contact with air is avoided or minimized in order to prevent oxidation. A solution comprising 44.8 ml $H_2O$, 6 ml $H_2SO_4$ (96.4%), and 23.0 ml $CH_3CN$, at approximately 40° C, is added to the wet acetylide in flask 62 through solution inlet port 74. Prior to this step, argon is introduced through gas inlet port 72 at a low flow rate to remove all oxygen. The acetylide dissolves completely within 25 minutes at 40 ± 2° C to give a light, yellowish clear solution. The acetylene produced from the dissolution of the acetylide in flask 62 is carried from the flask in the argon stream through refluxing condenser 64 and may be scrubbed as desired in either of the two acetylene scrubbing systems 66.

When the dissolution is complete, the outflow of gas is switched from the refluxing condenser 64 to the spiral condenser 68. The temperature in the water bath is increased in order to distil off the acetonitrile from the cuprous solution, and the cuprous ions are thus disproportionated into copper metal and cupric ions.

An azeotrope, $CH_3CN:H_2O$ = 83.7:16.3, boils at 76.5° C. The heating of flask 62 continues until the temperature reaches 89° C at which point the condensate is collected (32 ml). The solution remaining in flask 62 (66 ml) contains 2.051 g of $Cu^{++}$. The copper metal is collected by filtration, washed with water, acetone, and finally benzene, and thereafter dried under argon.

To determine the total amount of copper metal produced, the empty flask 62 is rinsed with water and then a solution of $HNO_3$ is used to dissolve any copper that adheres to the walls. The concentration of copper in this solution is determined by atomic absorption, and the total weight of copper recovered is calculated by adding the weight of the copper in this solution to the copper powder collected. Total copper metal produced under the above conditions is 1.899 g.

EXAMPLE 2

A synthetic ammoniacal solution having a pH of 9.7 is prepared containing the following:

10.0 g/l Cu (as carbonate)
0.501 g/l Ni (as carbonate)
0.489 g/l Co (as carbonate)
0.508 g/l Zn (as nitrate)
0.490 /l Cd (as nitrate)
2 ppm Pb (as chloride)
50 g/l $(NH_4)_2CO_3$
75 g/l $NH_4OH$ 800 ml of the above solution is reduced with carbon monoxide in flask 22, as described in Example 1, using a 2.12 g piece of copper wire as an initiator.

400 ml of this reduced solution, containing 4.21 g $Cu^+$ and 0.0013 g $Cu^{++}$, is transferred through conduit 40 to flask 44, and the cuprous ions are precipitated with acetylene gas at 30° C as described above. The acrytlide slurry is filtered. The filtrate, having a volume of 374.3 ml, is collected and analyzed by atomic absorption to determine the concentration of metals in solution. It contains:

0.0024 g Cu
0.1873 g Ni
0.1861 g Co
0.1899 g Zn
0.1830 g Cd
1 ppm Pb.

The cuprous acetylide precipitate is repulped with 100 ml $H_2O$ and refiltered under an argon atmosphere. 20.15 g of the filter cake is transferred into flask 62 and then a solution consisting of 31.5 ml $H_2O$, 16.5 ml $CH_3CN$, and 4.7 ml $H_2SO_4$ (96.4%) is added through solution inlet 74. The acetylide is completely dissolved within 20 minutes at 40° C. After the dissolution, the flask is switched from the reflux condenser mode to the spiral condenser mode, and the temperature within the flask is raised to distill off the acetonitrile and thus precipitate copper metal. This distillation is terminated when the temperature reaches 90° C. 20 ml of $CH_3CN/H_2O$ are condensed and collected in the collection flask 81.

The amount of copper metal collected by filtration and from the walls of flask 62 is 1.3240 g. Analysis by mass spectroscopy shows the following level of contamination of the copper powder:

Ni: 0.1 ppm
Cd: <1 ppm
Pb: 0.2 ppm
Co: 0.01 ppm
Zn: 0.1 ppm

EXAMPLE 3

Manganese deep sea modules are reduced and the metal values in the modules are leached with an aqueous ammoniacal leach solution according to the procedure disclosed in U.S. Pat. No. 3,983,017. After leaching of the nodules, the concentration of various metals in solution is adjusted to the following values:

6.5 g/l copper 7.2 g/l nickel
1.925 g/l cobalt
0.01 g/l manganese

One liter of the above solution in introduced into flask 22, heated to 47° C and adjusted to a pH of 10.3 by introducing ammonia and/or carbon dioxide through gas inlet 34 as needed. A small amount of copper powder is introduced into flask 22 in order to initiate the reduction of cupric ions by carbon monoxide as well as to incerease the final copper concentration in solution. The cuprous ion concentration reaches a value of about 8 g/l within 50 minutes.

Approximately 625 ml of the cuprous containing solution is then transferred through conduit 40 into flask 44 and cuprous acetylide is precipitated as described in Example 1. After the acetylide cake is washed on the filter with 200 ml of water at pH 10 ($NH_4OH$ added), a 21.889 g portion of the filter cake is transferred into flask 62 where it is dissolved with 34 ml of $H_2O$, 17.5 ml $CH_3CN$, and 4.25 ml $H_2SO_4$ (96.5%). The acetylide is completely dissolved within 30 minutes. The temperature reaches 59° C. After switching to the coil condenser as described previously, the temperature in the flask is raised to 91° C to distil off the acetonitrile and precipitate copper metal. The copper metal, collected by filtration and determined as set forth in Example 1, has a mass of 1.4006 g. The filtrate contains 1.593 g $Cu^{++}$, 0.00013 g nickel. and 0.0009 g cobalt. Analysis by mass spectroscopy of the copper powder indicates a nickel content of 0.3 ppm, a cobalt content of 0.02 ppm, a manganese content of 0.2 ppm, and a molybdenum content of 0.6 ppm.

EXAMPLE 4

The following experiment may be performed to determine the recoverability of acetylene upon dissolution of cuprous acetylide with a solution containing acetonitrile and sulfuric acid.

Cuprous acetylide is precipitated from an ammoniacal cuprous solution as described above and the acetylide is collected by filtration and washed with water under an argon atmosphere. A sample of the acetylide filter cake containing approximately 1.5 g of copper is transferred to flask 62 as quickly as possible in order to avoid prolonged contact with air. Argon introduced through gas inlet port 72 maintains an inert atmosphere within flask 62. A solution consisting of 25 ml of water and 5 ml of acetonitrile is added to the acetylide through solution inlet port 74 and the temperature is maintained at 40° C. when thermal equilibrium is obtained, a mixture of 24 ml $H_2O$, 8 ml $H_2SO_4$, and 8 ml $CH_3CN$ at 40° C is added in order to dissolve the acetylide. Argon gas which acts as a carrier for the acetylene produced by the hydrolysis, passes through the reflux condenser 62 and then through the acetylene scrubbers. One scrubber system collects all acetylene evolved up to a temperature of 43° C. The other system recovers the last traces of acetylene evolved between 43° and 84° C. When the total collected acetylene is determined quantitatively, 96.44% of the total amount theoretically present is collected. The small loss is believed to be due to the formation of carbonaceous materials which result from decomposition, polymerization etc.

In the embodiment of FIG. 1, the only consumable reagents are carbon monoxide and hydrogen gas in approximately 2:1 molar ratio. Synthesis gas containing approximately 2:1 molar ratio of carbon monoxide and hydrogen can be obtained from coke and steam or by partial oxidation of fuel oil and can be used in the process of the present invention. Acetylene, acetonitrile, sulfuric acid, and a solid hydrogenation catalyst are employed in a closed system, and hence are not consumed, although some make-up of inevitable small losses, when the process is practiced on an industrial scale, will be necessary. As can be appreciated from the above, the air form of energy consumed for the separation and reduction to coppermetal is the thermal emergy employed in disproportionation.

The copper metal obtained by employing the process of this invention is of very high purity since copper is first selectively separated as cuprous acetylide from basic solutions, and thereafter selectively recovered via disproportionation of $Cu^+$.

The acetylene/acetylide intermediate couple has multiple function and advantages insofar as it quantitatively and selectively separates copper from basic solutions as a solid, hence greatly concentrating the copper and providing a first purification step. Its use enables the metal of interest to be transferred from a dilute basic to concentrated acid system without direct acid-base contact, thus avoiding neutralization and consequent reagent loss. This acetylide intermediate also makes it possible to exchange cuprous ion ligands from ammonia to aceto-nitrile. Direct exchange is both theoretically and practically impossible. Further, acetylene regeneration provides the means of preventing a hydrogen ion buildup in the acidic side of the process since it transfers protons from the acidic to the basic circuit of the process, and it introduces no impurities into the system and is not consumed.

Incomplete washing of the cuprous acetylide which would result in carry over of ammonia, nickel, cobalt, carbonate, etc., the products of side reactions in the copper recovery circuit, impurities entering with the gases that react with the various solutions, and normal contamination of the process water are anticipated sources of contamination of the recovery circuit. Accordingly, a purge treatment may be necessary. One skilled in the art will, of course, have no difficulty in designing such a purge system.

From the foregoing, it should be apparent that the broad concept of the invention is to react a cuprous acetylide with an acid an a nitrile to form a soluble cuprous-nitrile complex. Although various preferred embodiments have been disclosed, there are many modifications which can be made. For example, the cuprous ions can be complexed prior to precipitation as the acetylide with a number of ligands. A representative list of such ligands includes: amines (straight chained or branched, soluble or insoluble), amides, pyridines, aniline (and derivatives) picolines, acetates or cuprous salts which are soluble in non aqueous basic media such as sulfoxides. It is preferred to precipitate the cuprous acetylide from an aqueous solution. However, it is possible to precipitate the acetylide from a non-aqueous solution. For instance, cuprous ions can be extracted into an inert organic solvent such as kerosene, long chain alcohols etc., containing a cuprous ion stabilizing ligand. The cuprous loaded organic phase can be separated from the aqueous phase and then a complex cuprous acetylide can be precipitated and separated from the organic phase. This precipitate can then be dissolved in an acidified aqueous nitrile solution to regenerate the acetylenic compound and form a cuprous nitrile complex suitable for disproportionation.

Acetylene is preferable overall; but, if R-CH≡CH is used, then it is preferable that the acetylenic compound (R-CH≡CH) be one in which the R is an alkyl group containing 1-5 carbon atoms. However, longer chain acetylenic compounds may be employed. For example, such compounds can be carried in an inert organic solvent such as kerosene or other hydrocarbons, benzene, long chained water insoluble alcohols, etc. Solid long chained resin-like acetylenic compounds can be utilized if immobilized on a solid support.

The acetylide can be reacted with any nitrile in the presence of an acid. The cuprous complex obtained from the acetylide hydrolysis can be disproportionated by thermal methods or by electrochemical methods. For example, when the cuprous acetylide is reacted with an acid and 2-hydroxy-cyanoethane, copper can be recovered by the one electron electrowinning process set forth in U.S. Pat.No. 3,937,675 by Parker et al entitled Electrowinning of Copper, the teachings of which are incorporated herewith by reference.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A process for producing copper metal from a solution containing $Cu^+$ ions comprising the steps of:
    a. precipitating the $Cu^+$ ions from the solution as a cuprous acetylide;
    b. separating the cuprous acetylide precipitate from the solution;
    c. reacting the cuprous acetylide with an acid and a nitrile to form a soluble cuprous-nitrile complex;
    d. removing the nirile from the complex and disproportionating the $Cu^+$ ion to produce copper metal and $Cu^{++}$ ions.

2. The process as set forth in claim 1 wherein step (a) is effected by passing gaseous $C_2H_2$ through anammoniacal solution of cuprous ions.

3. The process as set forth in claim 1 wherein step (a) is effected by passing an acetylenic compound having the formula $RC≡CH$, where R is an alkyl group having 1-6 carbon atoms, through an ammoniacal solution of cuprous ions.

4. The process as set forth in claim 1 wherein step (a) is effected by passing 3, 3 dimethyl-1-butyne through the solution.

5. The process as set forth in claim 1 wherein the nitrile reacted in step (c) is $CH_3CN$.

6. The process as set forth in claim 1 wherein a member selected from the group consisting of methanol, ethanol, acetone, and mixtures thereof is added to the cuprous-nitrile to form an azeotrope and to aid in the formation of the soluble nitrile in step (c).

7. The process as set forth in claim 1 wherein the solution of $Cu^+$ ions in step (a) comprises an aqueous ammoniacal solution containing the complex cuprous ammine ion $Cu(NH_3)_2^+$.

8. The process as set forth in claim 1 wherein said solution is a basic solution and contains an anion chosen from the group consisting of $OH^-$, $Cl^-$, $SO_4^=$, $NO_3^-$, $C_2H_3O_2^-$, $CO_3^=$, $PO_4^-$, $HCO_3^-$, $HPO_4^=$, $H_2PO_4^-$, and mixtures thereof.

9. The process as set forth in claim 8 wherein said solution contains the $SO_4^=$ anion.

10. The process as set forth in claim 1 wherein step (d) is effected by distillation of the cuprous-nitrile complex.

11. The process as set forth in claim 1 wherein an acetylenic compound is produced in step (c) and is reused in step (a).

12. The process as set forth in claim 1 wherein nitrile is produced in step (d) and is reused in step (c).

13. The process as set forth in claim 1 wherein in step (c) the cuprous acetylide is reacted with an acid and 2-hydroxy-cyanoethane and wherein in step (d) the copper metal is produced by one electron electrowinning.

14. The process as set forth in claim 13 wherein acid is produced during the electrowinning of step (d) and is reused in step (c).

15. The process as set forth in claim 14 wherein acid is produced during the electrowinning of step (e) and is reused to dissolve acetylide in step (d).

16. A process for producing copper metal from a solution containing $Cu(NH_3)_4^{++}$ comprising the steps of:
    a. reducing the $Cu(NH_3)_4^{++}$ to $Cu(NH_3)_2^+$;
    b. precipitating the $Cu^+$ from the $Cu(NH_3)_2^+$ ion as a cuprous acetylide;
    c. separating the cuprous acetylide from the solution;
    d. reacting the cuprous acetylide with an acid and a nitrile to form a cuprous nitrile complex;
    e. removing the nitrile from the complex to disproportionate the $Cu^+$ to produce copper metal and $Cu^{++}$ ions.

17. The process of claim 16 wherein step (a) is effected by contacting the $Cu(NH_3)_4^{++}$ with CO.

18. The process of claim 16 wherein step (b) is effected by passing gaseous $C_2H_2$ through the solution of cuprous ions.

19. The process of claim 16 wherein step (b) is effected by passing an acetylenic compound having the formula $RC≡CH$, where R is an alkyl roup having 1-6 carbon atoms, through the solution.

20. The process of claim 16 wherein step (b) is effected by passing 3, 3 dimethyl-1-butyne through the solution.

21. The process of claim 16 wherein the nitrile is $CH_3CN$.

22. The process of claim 16 wherein a substance chosen from the group consisting of methanol, ethanol, acetone, and mixtures thereof is added to the cuprous-nitrile to form an azeotrope and to aid in dissolution of acetylide in step (d).

23. The process of claim 16 wherein said solution is a basic solution and contains an anion chosen from the group consisting of $OH^{31}$, $Cl^{31}$, $SO_4^{30}$, $NO_3^{31}$, $C_2H_3O_2^{31}$, $CO_3^{32}$, $PO_4^{32}$, and mixtures thereof.

24. The process of claim 16 wherein step (e) is effected by distillation of the cuprous-nitrile complex.

25. The process of claim 16 wherein an acetylenic compound is produced in step (d) and is resued in step (b).

26. The process of claim 16 wherein nitrile is produced in step (e) and reused in step (d).

27. The process as set forth in claim 16 wherein in step (d) the cuprous acetylide is reacted with an acid and 2-hydroxy-cyanoethane and wherein in step (e) the copper metal is produced by one electron electrowinning.

28. A process for producing copper metal from a solution containing $Cu^{++}$ ions comprising the steps of:
 a. reducing the $Cu^{++}$ ions to $Cu^+$ ions in the presence of ammonia;
 b. precipitating the $Cu^+$ as $Cu_2C_2$;
 c. separating the $Cu_2C_2$ from the solution;
 d. reacting the $Cu_2C_2$ with acetonitrile and sulfuric acid to form a solution containing a cuprous acetonitrile complex;
 e. removing the acetonitrile from said complex in solution to disproportionate the $Cu^+$ and to form $Cu^o$ and $Cu^{++}$.

29. The process of claim 28 wherein step (a) is effected by passing CO through the solution.

30. The process of claim 28 wherein step (b) is effected by passing $C_2H_2$ through the $Cu^+$ containing solution.

31. The process of claim 28 wherein $C_2H_2$ is produced in step (d) and reused in step (b).

32. The process of claim 28 wherein acetonitrile is produced in step (e) and reused in step (d).

* * * * *